(12) United States Patent
Maynard et al.

(10) Patent No.: US 7,786,213 B2
(45) Date of Patent: Aug. 31, 2010

(54) BIOMACROMOLECULE POLYMER CONJUGATES

(75) Inventors: Heather D. Maynard, Los Angeles, CA (US); Debora Bontempo, Mainz (DE)

(73) Assignee: The Regents Of The University Of California, Oakland, CA (US)

( * ) Notice: Subject to any disclaimer, the term of this patent is extended or adjusted under 35 U.S.C. 154(b) by 0 days.

(21) Appl. No.: 10/576,038

(22) Filed: Feb. 2, 2007

(65) Prior Publication Data

US 2007/0276088 A1 Nov. 29, 2007

Related U.S. Application Data

(63) Continuation-in-part of application No. PCT/US2004/033125, filed on Oct. 7, 2004.

(60) Provisional application No. 60/511,752, filed on Oct. 15, 2003.

(51) Int. Cl.
*A61K 47/48* (2006.01)
*A61K 9/16* (2006.01)
*C08L 89/00* (2006.01)
*C08B 37/00* (2006.01)

(52) U.S. Cl. .................... 525/54.1; 527/201; 527/202

(58) Field of Classification Search ............... 525/54.1; 527/201, 207
See application file for complete search history.

(56) References Cited

U.S. PATENT DOCUMENTS

| | | | |
|---|---|---|---|
| 3,806,417 A | 4/1974 | Hochstetter et al. | |
| 4,806,610 A | 2/1989 | Erickson et al. | |
| 4,822,867 A | 4/1989 | Erhan et al. | |
| 5,035,997 A * | 7/1991 | Oster et al. | 435/6 |
| 5,207,941 A | 5/1993 | Kroner et al. | |
| 5,260,396 A | 11/1993 | Kroner et al. | |
| 5,444,150 A * | 8/1995 | Inman et al. | 530/300 |

(Continued)

FOREIGN PATENT DOCUMENTS

| | | |
|---|---|---|
| DE | 4108170 | 9/1992 |
| DE | 10238176 | 3/2004 |
| EP | 0263658 | 4/1988 |
| FR | 2655048 | 5/1991 |

OTHER PUBLICATIONS

Matyjaszewski et al., Atom Transfer Radical Polymerization, Chem. Rev. 2001, 101, 2921-2990.*

(Continued)

*Primary Examiner*—Mark Eashoo
*Assistant Examiner*—Liam J Heincer
(74) *Attorney, Agent, or Firm*—Koppel, Patrick, Heybl & Dawson; Michael J. Ram

(57) ABSTRACT

Chemical polymerization procedures initiated by, and proceeding from, a biomolecule, particularly a protein, for the formation of biomolecule-polymer conjugates, particularly protein-polymer conjugates, which have therapeutic uses, are intermediates for forming other materials or are usable in diagnostic sensors are disclosed. Polymerization can be initiated by a protein in the absence of additional initiation agents to form the protein-polymer conjugate. Alternatively, polymerization is initiated in the presence of an additional initiation agent that does not interact with the protein. Amino acids existing in the protein can serve as the sites for initiation of the polymerization or the protein can be modified to contain site(s) for initiation or protein with active sites can be prepared by recombinant methods, chemical ligation, solid-phase synthesis, or other techniques to generate site(s) for initiation.

8 Claims, 8 Drawing Sheets

U.S. PATENT DOCUMENTS

| | | | | |
|---|---|---|---|---|
| 5,482,996 | A * | 1/1996 | Russell et al. | 525/54.1 |
| 5,505,952 | A * | 4/1996 | Jiang et al. | 424/423 |
| 5,523,348 | A * | 6/1996 | Rhee et al. | 525/54.1 |
| 5,527,527 | A * | 6/1996 | Friden | 424/178.1 |
| 5,789,487 | A * | 8/1998 | Matyjaszewski et al. | 525/301 |
| 5,998,588 | A * | 12/1999 | Hoffman et al. | 530/402 |
| 6,007,833 | A * | 12/1999 | Chudzik et al. | 424/425 |
| 6,156,345 | A * | 12/2000 | Chudzik et al. | 424/484 |
| 6,221,958 | B1 * | 4/2001 | Shalaby et al. | 525/54.1 |
| 6,251,382 | B1 * | 6/2001 | Greenwald et al. | 424/78.17 |
| 6,251,680 | B1 * | 6/2001 | Fu et al. | 436/56 |
| 6,291,582 | B1 * | 9/2001 | Dordick et al. | 525/54.1 |
| 6,433,078 | B1 * | 8/2002 | Gololobov et al. | 525/54.1 |
| 6,492,460 | B2 * | 12/2002 | Haq et al. | 525/50 |
| 6,495,657 | B1 * | 12/2002 | McDonald et al. | 528/310 |
| 6,689,844 | B2 * | 2/2004 | Roos et al. | 525/382 |
| 6,727,323 | B2 * | 4/2004 | Weiler | 525/344 |
| 6,994,964 | B1 * | 2/2006 | Chang et al. | 435/6 |
| 7,018,624 | B2 * | 3/2006 | Harris | 424/78.3 |
| 7,057,019 | B2 * | 6/2006 | Pathak | 530/362 |
| 7,153,821 | B2 * | 12/2006 | Blokzijl et al. | 510/475 |
| 2002/0143127 | A1 * | 10/2002 | Coca et al. | 526/172 |
| 2003/0220447 | A1 * | 11/2003 | Harris | 525/54.1 |
| 2004/0044156 | A1 * | 3/2004 | Haddleton | 526/172 |
| 2004/0086992 | A1 * | 5/2004 | Harris et al. | 435/174 |
| 2004/0142171 | A1 * | 7/2004 | Bottcher et al. | 428/402.22 |
| 2004/0235734 | A1 * | 11/2004 | Bossard et al. | 514/12 |
| 2005/0027070 | A1 * | 2/2005 | Rhee et al. | 525/54.1 |
| 2005/0042612 | A1 * | 2/2005 | Hubbard et al. | 435/6 |
| 2005/0059129 | A1 * | 3/2005 | Park | 435/189 |
| 2005/0123501 | A1 * | 6/2005 | Lewis | 424/78.3 |
| 2005/0147581 | A1 * | 7/2005 | Zamiri et al. | 424/78.27 |
| 2005/0163743 | A1 * | 7/2005 | Lewis et al. | 424/78.3 |
| 2006/0057180 | A1 * | 3/2006 | Chilkoti et al. | 424/422 |
| 2007/0083006 | A1 * | 4/2007 | Hinds et al. | 525/54.1 |

OTHER PUBLICATIONS

Bontempo et al., J. Am. Chem. Soc. 2004, 126, p. 15372-73.*
Kiick, K.L. et al., "Expanding the Scope of Protein Biosynthesis by Altering the Methionyl-tRNA Synthetase Activity of a Bacterial Expression Host", *Angew. Chem., Int. Ed.*, 39, p. 2148-2152 (2000).
Kiick, K.L. et al., "Identification of an Expanded Set of Translationally Active Methionine Analogues in *Escherichia coli*", *FEBS Lett.*, 502, p. 25-30 (2001).
Kochendoerfer, G.G. et al., "Design and Chemical Synthesis of a Homogeneous Polymer-Modified Erythropoiesis Protein", *Science*, 299, p. 884-887) (2003).
Wang Y. et al., "Structural and Biological Characterization of Pegylated Recombinant Interferon Alpha-2b and its Therapeutic Implications", *Adv. Drug Delivery Rev.*, 54, p. 547-570 (2002).
Kinstler, O., "Mono-N-terminal Poly(ethylene glycol)-Protein Conjugates", *Adv. Drug Delivery Rev.*, 54, p. 477-485 (2002).
Chapman, A.P., et al. "Therapeutic Antibody Fragments with Prolonged In Vivo Half-Lives", *Nat. Biotechnol*, 17, p. 780-783 (1999).
Duncan, R., "The Dawning Era of Polymer Therapeutics", *Nat. Rev. Drug Discovery*, 2, p. 347-360 (May 2003).
Hannink, J.M., "Protein-Polymer Hybrid Amphiphiles", *Angew. Chem., Int. Ed.*, 40, p. 4732-4734 (2001).
Bontempo, D. et al., "Protein Macroinitiators for Atom Transfer Radical Polymerization", *Polymer Preprints*, 46(1), p. 78-79 (2005).
Heredia, K. L. et al., "In-Situ Preparation of Bovine Serum Albumin-poly (PEG Methacrylate) Conjugates", *Polymeric Materials Science & Engineering*, 94, p. 354-355 (2006).
Lele, Bhalchandra S. et al., "Synthesis of Uniform Protein-Polymer Conjugates", *Biomacromolecules*, 6, No. 6, p. 3380-3387 (2005).
Heredia, K. L. et al., "In Situ Preparation of Protein—'Smart' Polymer Conjugates with Retention of Bioactivity", *J. Am. Chem. Soc.*, 127, 16955-16960 (2005).
Heredia, K. K. et al., Supporting Information, "In Situ Preparation of Protein—'Smart' Polymer Conjugates with Retention of Bioactivity", p. S1-S12.
Bontempo, D. et al., Steptavidin as a Macroinitiator for Polymerization: In Situ Protein—Polymer Conjugate Formation, *J. Am. Chem. Soc.*, 127, No. 18, 6508-6509 (2005).
Bontempo, D. et al., Supporting Information, "Streptavidin as a Macroinitiator for Polymerization: In Situ Protein-Polymer Conjugate Formation".
Lele, Bhalchandra, "Synthesis of Uniform Protein-Polymer Conjugates", Biomacromolecules, vol. 6, No. 6, 3380-3387 (Oct. 4, 2005).

* cited by examiner

A: BSA

B: BSA-polymer conjugate

BIOMACROMOLECULE POLYMER CONJUGATES

This application claims benefit of, and is a Continuation-in-part of PCT/US2004/033125 filed Oct. 7, 2004, which has a priority date, based on U.S. Provisional Application 60/511,752, of Oct. 15, 2003. This invention relates to the formation of protein-polymer conjugates which have therapeutic uses, are intermediates for forming other materials or are usable in diagnostic sensors.

BACKGROUND

Complexes between synthetic polymers and biological macromolecules can provide important commercial therapeutics as well as valuable building blocks of structured materials and sensors. For example, conjugation of therapeutic proteins with polymers, such as with polyethylene glycol, has been shown to prolong the serum half-life and reduce immunogenicity of the proteins. Conjugates of biomacromolecules covalently linked to synthetic polymers at the ends of the synthetic polymers are examples of such complexes. In this instance, controlling the site of covalent conjugation on the biomacromolecule, the number of polymer chains conjugated, and the length, dispersity, and architecture of the synthetic polymer chains are particularly critical to resultant properties.

The currently used method to prepare covalent biomacromolecule-polymer complexes involves first preparing a polymer chain modified with a reactive end group and subsequently conjugating that preformed polymer to the biomacromolecule which contains either a natural or a non-natural amino acid. Kiick, K. L. et al. ("Expanding the Scope of Protein Biosynthesis by Altering the Methionyl-tRNA Synthetase Activity of a Bacterial Expression Host", *Angew. Chem., Int. Ed.*, 39 (2000) p2148-2152; "Identification of an Expanded Set of Translationally Active Methionine Analogues in *Escherichia Coli*", *FEBS Lett.*, 502 (2001) p25-30) discusses the incorporation of non-natural amino acids into proteins.

U.S. Pat. No. 5,998,588 to Hoffman et al. is one example of several patents issued to Hoffman covering various procedures for the conjugation of preformed polymer chains to numerous biomolecules including proteins.

Kochendoerfer, G. G. et al. ("Design and Chemical Synthesis of a Homogeneous Polymer-Modified Erythropoiesis Protein", *Science*, 299 (2003) p884-887) gives an example of the formation of a polymer modified protein by chemical synthesis, an amino-oxy group on the polymer being linked at ketone bearing Lys (N-levulinyl) residues on the peptide.

Wang Y. et al. ("Structural and Biological Characterization of Pegylated Recombinant Interferon Alpha-2b and its Therapeutic Implications", *Adv. Drug Delivery Rev.*, 54 (2002) p547-570) discusses the therapeutic use of small proteins (type 1 interferon alpha) as anti-infectives and anti-tumor agents. However, the utility of such therapy is limited by the half-life of interferon and its rapid clearance from the body. The efficacy of interferon can be improved (i.e., converted to a long acting agent) by reacting the protein with mono-methoxy polyethylene glycol to form pegylated interferon (PEG Intron®), a covalent conjugate of IFN-$\alpha_{2b}$ linked to a 12,000 Da PEG molecule. Pegylation occurs at any or all of numerous nucleophilic sites in the protein (the s-amino groups of the 10 lysines, the $\alpha$-amino group at the N-terminal cysteine, the imidazolyl nitrogens of the three histidines and the hydroxyl groups at the 14 serine, 10 threonines, and 5 tyrosines). Because of the numerous potential reaction sites, a heterogeneous mixture of various different modified proteins is produced.

Kinstler, O. ("Mono-N-terminal Poly(ethylene glycol)—Protein Conjugates", *Adv. Drug Delivery Rev.*, 54, (2002) p477-485) also reports on the formation of PEG-protein conjugates. They maximize the selectivity of the PEG aldehyde conjugation to the N-terminus of an unprotected polypeptide chain by taking advantage of the differences between $pK_a$ values of the $\alpha$-amino group of the N-terminal amino acid residue and the $\epsilon$ amino group of the Lys residues in the peptide backbone.

Another approach is to target cysteine thiols using a polymer (PEG) activated with maleimides, vinyl sulfones, pyridyl disulfides, or other compounds reactive to thiols, thus taking advantage of the scarcity of free cysteines in proteins. Chapman, A. P., et al. ("Therapeutic Antibody Fragments with Prolonged In Vivo Half-Lives", *Nat. Biotechnol,* 17 (1999) p780-783) (referenced in Kinstler et al.).

The state of the art regarding polymeric drugs, polymer-drug conjugates, polymer-protein conjugates, polymeric micelles with covalently bound drugs and multi-component complexes is reviewed by Duncan, R. ("The Dawning Era of Polymer Therapeutics", *Nat. Rev. Drug Discovery,* 2, (May 2003) p347-360). Described are conjugates formed by reacting the polymer with the biomolecule. The polymeric materials identified include PEG, N-(2-hydroxypropyl)methacrylamide (HPMA) copolymers, poly(vinylpyrrolidone) (PVP), poly(ethyleneimine) (PEI), polyamidoamines (DIVEMA), natural polymers including dextran, hyaluronic acid, chitosans and synthetic polyamino acids such as poly(L-lysine), poly(glutamic acid), poly(malic acid) and poly(aspartamides).

Hannink, J. M. ("Protein-Polymer Hybrid Amphiphiles", *Anew. Chem., Int. Ed.,* 40, (2001) p4732-4734) discloses the irreversible association of two molecules of monobiotinylated polymers with streptavidin to form an amphiphilic protein-polymer hybrid.

Unfortunately, synthesis of the polymers with reactive end groups and separation of the excess (unreacted) polymer chains from the conjugate formed between the polymer and biomolecule is difficult and time consuming. In addition, many of these methods are not quantitative or specific and do not allow for control over the placement and number of polymer chains. To make these conjugates available, a simple and effective preparation of biomacromolecule-polymer complexes is needed.

BRIEF DESCRIPTION

The present invention generally relates to chemical polymerization initiated by, and proceeding from, a protein. In one embodiment of the invention, polymerization is initiated by a protein in the absence of additional initiation agents forming the protein-polymer conjugate. In another embodiment, polymerization is initiated in the presence of an added initiation agent that does not interact with the protein. In this case, during the polymerization process some polymer not attached to the protein is also formed. Removal of this unbound polymer results in the purified protein-polymer conjugate. The protein can be modified to contain site(s) for initiation or prepared by recombinant methods, chemical ligation, solid-phase synthesis, or otherwise with site(s) for initiation. Examples of the preparation of the conjugate are shown by the formation of poly(N-isopropylacrylamide)-bovine serum albumin conjugates in the presence or absence of a solid supported initiator and poly(N-isopropylacrylamide)- lysozyme conjugates and conjugates of poly(N-isopropylacrylamide) or poly(ethylene glycol) methyl ether methacrylate (PEGMA) and streptavidin prepared in the presence of a solid supported initiator.

Currently, protein-polymer conjugates are prepared by synthesizing telechelic polymers (end group modified polymers) and by reaction of these polymers with proteins. This takes many steps and the products produced are difficult to purify. In a procedure incorporating features of the invention polymers are prepared by polymerizing monomers using proteins modified with initiation sites, resulting in the formation of the protein-polymer conjugate directly. This greatly simplifies the purification procedures because the conjugates are then purified from the small monomer molecules and not from large polymer chains. It also reduces the preparation steps since there is no need for end-functionalization of the polymers, and the procedure is applicable to a wide range of proteins and hydrophilic or hydrophobic monomers. A still further advantage of this approach is that the characterization of the end product is more facile. It is significantly easier to determine where small fragments, such as initiator sites, are located on a protein, then to determine where a polymer chain is attached and how many are attached. As long as the polymer is attached to the site of the initiator fragment and the initiator fragment site does not migrate during the polymerization, the attachment site of the polymer can be inferred from characterization of the protein initiator. Additionally, control over the number and placement of the polymer chains on the amino acid sequence could be achieved using established protocols for site-specific modification of proteins with the initiator fragment or by expressing recombinant proteins displaying artificial amino acids containing the initiator fragment.

More specifically in a preferred embodiment for conjugating a protein:
a) An initiator is added to the protein to provide the initiating site on the protein. An assortment of natural or artificial amino acids may be employed as an anchoring point for the initiator.
b) Cysteine residues naturally or artificially present on the protein are an example of anchoring points to modify the protein with the initiator; nevertheless, the invention is not restricted to the presence of cysteines on proteins. Other natural or artificial amino acids, or non-covalent interactions, can be used to conjugate the molecule that will initiate the polymerization from the protein.
c) A protein modified with the initiator is mixed with the monomer with or without added catalyst to initiate the polymerization of the monomer from the protein forming the protein-polymer conjugate in situ.

DETAILED DESCRIPTION

The present invention generally relates to a process for the chemical polymerization initiated from biomolecules to form biomolecule-conjugates, particularly proteins to form protein-polymer conjugates, and the compositions prepared by that process. The protein can be modified with an agent or agents that can initiate polymerization, or be prepared containing modified sites or modified by other techniques so that it can react with the monomer, or the protein can be modified to contain one or more sites for initiation, or protein with active sites can be prepared by recombinant methods, chemical ligation, solid-phase synthesis, or other techniques to generate site(s) for initiation. Chemical initiation and polymerization results in a protein-polymer conjugate with the initiator as a link between the protein and the polymer. Polymerization can occur with or without addition of non-interacting initiators.

As an example, the protein can be modified with an initiator either covalently bound or which forms an affinity complex with the protein. For example, bovine serum albumin (BSA) can be modified using an initiator to form a disulfide bond with a free cysteine in the BSA. In another example a mutant lysozyme can be modified through a disulfide bond or through reaction of the free cysteine with a maleimide functionalized initiator. However, other chemistries such as the Michael-type addition with vinyl sulfone modified initiators can be also used. As a further example, a biotinylated initiator can be synthesized and conjugated via affinity interactions to the protein streptavidin. Modification by conjugation to other amino acids, such as lysines, arginines, histidines, serines, threonines, aspartic acids, glutamic acids, or artificial amino acids, or the ends of the protein or by other affinity interactions may also be used.

All of the initiators in the examples initiate radical polymerization, specifically atom transfer radical polymerizations (ATRP). However, other molecules that initiate radical, cationic, anionic, or metathesis polymerizations may be employed as initiators and other radical-based polymerization techniques can be used. Using this technique a large number of protein-polymer complexes can be formed quickly. Described below are complexes of albumin, lysozyme, and streptavidin with poly(N-isopropylacrylamide) (poly(NIPAAm)). Another embodiment uses ethylene glycol methacrylate as the monomer, forming a conjugate including poly(ethylene glycol methacrylate) (PEGMA). However, other polymers including, for example, polyesters, poly(meth)acrylamides, poly(meth)acrylates, polyethers, or polystyrenes can be produced using the techniques described herein. An advantage of using a controlled polymerization technique such as ATRP is the possibility of producing polymers with narrow molecular weight distributions.

Figure 13:
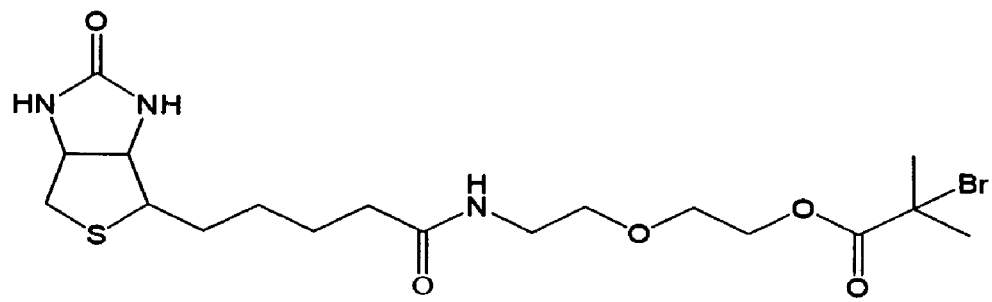
FIG. 13 shows the chemical structure of a biotinylated initiator.

Polymer formation may be conducted using modified biomolecules, particularly modified proteins as initiators. Compared to the current state of the art, this method has many advantages. Placement (location) and number of polymer chains is critical for properties, but difficult to control by current techniques. The process described herein readily allows the placement and number of polymer chains to be defined by the placement and number of initiating fragment(s). As an example, the albumin protein was modified at one or three sites with the initiator. As another example, lysozyme was modified at one site with initiator. In another example, streptavidin, which has four binding sites for biotin, was modified with the biotinylated initiator shown in FIG. 13 at three of the four sites. In addition, proteins may be prepared with defined placement and number of initiation sites by incorporation of artificial amino acids capable of initiating polymerization. For comparison, preparation of protein-polymer complexes by current techniques is more time consuming because a telechelic polymer with suitably reactive end groups must first be prepared. The polymer is then reacted with the protein and excess polymer is separated from the protein-polymer complex. Modification of biomolecules with small molecules is more efficient and the resulting complexes are easy to purify because the polymer is formed in situ attached directly to the protein. Further, it is easier to identify and locate the initiator sites on a protein, and react these identified locations with monomers then to first form the polymer and determine the sites of conjugation between the protein and the polymer, after conjugation is complete. In addition, the technique described in this invention is flexible. For example, it is difficult and time consuming to attach a preformed hydrophobic polymer to a hydrophilic protein, whereas polymerization of a hydrophobic monomer attached to a protein is more facile.

Uses of biomolecule-polymer conjugates prepared by initiation and polymerization from, for example, proteins include, but are not limited to, use as human therapeutics, in proteomics, as protective coatings, in composite or smart materials, and in sensors. Currently there are several protein-polymer conjugates formed by prior techniques on the market or in clinical development as human therapeutics. Polymer modification of proteins provides significant clinical benefits, including increased pharmacokinetic properties. Protein-polymer conjugates can be utilized in protein array chips for proteomics applications. Conjugates, where the protein responds to stimuli and the polymer provides material stability, can be useful in protective coatings and/or clothing, and as composite materials. An example of use as a sensor material includes protein-polymer conjugates that respond to bioterrorism agents or small molecules to give a detectable color changes and/or signals. The biomolecule-conjugates present in bulk, organized on the surface of a carrier or formed into micelles or liposomes, can also be used as drug delivery agents capable of selectively targeting specific tissue within the body.

The following examples, describing polymerization from albumin (Examples 1 and 2), from an enzyme lysozyme (Example 3) and from streptavidin (Example 4), are presented for the purpose of illustration only and not intended in anyway to limit the scope of the present invention. The approach was first explored using BSA for several reasons. BSA is readily available in larger quantities than most proteins, thus providing the flexibility to explore the polymerization conditions and generate enough bioconjugate to cleave and isolate the resultant polymer. BSA also contains a free surface cysteine at amino acid 34. The technique and characterization of the conjugate was confirmed with BSA prior to using the disclosed procedure on a mutant lysozyme to demonstrate retention of biological activity of the conjugate.

Example 1

Polymerization from Modified Bovine Serum Albumin

To explore the approach, proteins were modified at free cysteine residues and the conjugates were formed. This amino acid was targeted because well-defined bioconjugates have been prepared in the past by reacting preformed polymer chains with free cysteines that exist naturally or are placed in mutant forms of proteins. Therefore, polymerizing from proteins modified at cysteine residues presented a general strategy to produce protein-polymer conjugates and provided the opportunity to modify proteins at specific positions as well as prepare materials for direct comparison with conjugates prepared by these prior techniques.

Figure 1:
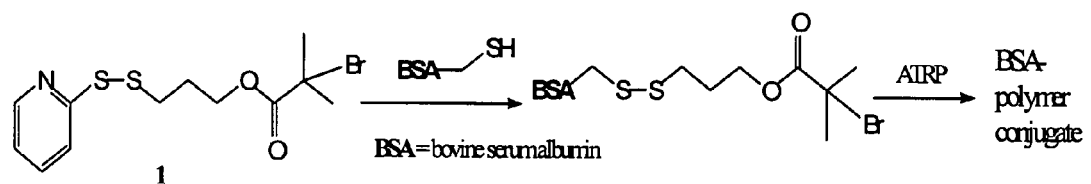
FIG. 1 shows a reaction scheme for modification of bovine serum albumin (BSA) with an initiator fragment and polymerization from the bovine serum albumin that has been modified with an initiator.

FIG. 1 shows the reaction scheme to produce a modified BSA and then a polymer conjugate of that modified protein. Bovine serum albumin (BSA) was modified at a single site to enable the polymerization directly from the albumin. A single free cysteine within the protein was modified to have a bromoisobutyrate functionality suitable for initiation of radical polymerization as shown in FIG. 1. The initiator precursor, propyl-mercaptopyridine 2-bromoisobutyrate (1) reacts efficiently with any protein, enzyme, or antibody that, naturally or by engineering, contains a free cysteine, and thus represents a general approach. Mass spectrometry analysis of the resulting BSA initiator (BSA-I) demonstrated that the albumin was modified with no more than one molecule of initiator per BSA molecule.

Figure 2:
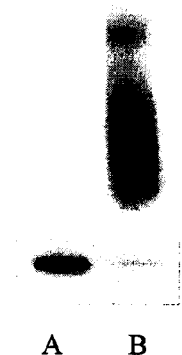
FIG. 2, shows the gel electrophoresis separation, visualized by coomassie staining, of the protein bovine serum albumin (Column A) and the protein-polymer conjugate formed by polymerization from the BSA-initiator (BSA-I) complex (Column B) using the reaction scheme of FIG. 1.
Figure 3:
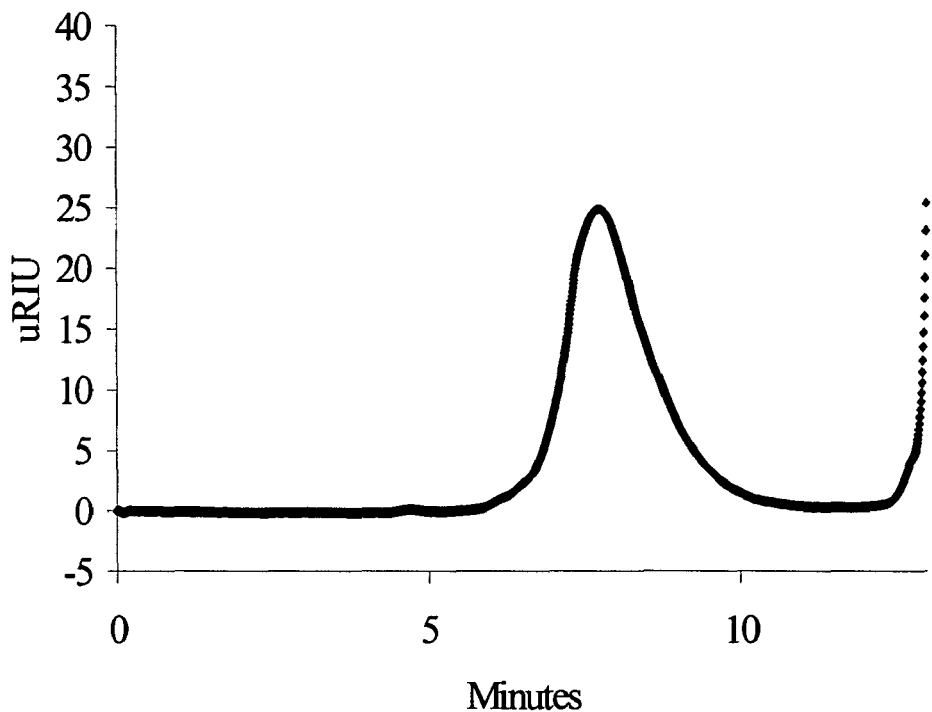
FIG. 3 is a graph showing the gel permeation chromatograph trace for poly(NIPAAm) formed using modified BSA (BSA-I) as an initiator using the reaction scheme of FIG. 1.

Polymerization was then accomplished using a radical polymerization technique (atom transfer radical polymerization, ATRP) that can result in polymers with narrow molecular weight distributions and programmed molecular weights. BSA-poly(NIPAAm) conjugates were prepared as an example using standard ATRP polymerization conditions. Polymerization to form the conjugate is evidenced by the higher molecular weight of the conjugate (Column A of FIG. 2) compared to BSA (Column B of FIG. 2) as determined by gel electrophoresis. The polymer was conjugated to the protein via a disulfide bond. To demonstrate that the polymerization occurred, this bond was chemically reduced and the poly(NIPAAm) generated by polymerization from the protein was isolated. Characterization of the polymer, conducted by proton nuclear magnetic spectroscopy and infrared spectroscopy, proved the poly(NIPAAm) identity. Gel permeation chromatography confirmed that a polymer had been synthesized (FIG. 3). As expected, identical polymerization conditions using unmodified BSA, did not result in formation of a polymer.

Synthesis of propyl-mercaptopyridine 2-bromoisobutyrate (1). Hydroxypropyl-mercaptopyridine (0.50 g, 2.5 mmol), 1,3-dicyclo-hexylcarbodiimide (DCC, 0.516 g, 2.5 mmol) and 4-dimethylaminopyridine (DMAP, 0.031 g, 0.25 mmol) were dissolved in 20 mL of dry, dichloromethane. 2-Bromo-2-methylpropionic acid (0.414 g, 2.5 mmol) was added and the reaction mixture was stirred overnight at room temperature. The reaction mixture was filtered, the solvent evaporated under vacuum and the oily residue purified by column chromatography (hexanes:ethyl acetate 60:40) to generate propyl-mercaptopyridine 2-bromoisobutyrate (1) with a yield of 53%.

Conjugation of propyl-mercaptopyridine 2-bromoisobutyrate (1) to bovine serum albumin (BSA). 13 mg of propyl-mercaptopyridine 2-bromoisobutyrate (1) prepared as indicated above were dissolved in 1 mL of DMSO and added drop wise to a solution of BSA (2 g) in deionized, distilled water (36 mL). The mixture was incubated overnight at room temperature. After centrifuging out the insoluble residue, the product (BSA-propyl 2-bromoisobutyrate, BSA-I) was purified by dialysis and recollected after lyophilization.

Polymerization of BSA-propyl 2-bromoisobutyrate from large amounts of proteins. A Schlenk tube was charged with N-isopropylacrylamide (NIPAAm, 200 mg, 1.77 mmol) and BSA-I (400 mg). It was then evacuated and refilled with argon three times. 2 mL of degassed water were used to solubilize the monomer and the initiator. A catalyst stock solution was prepared by dissolving CuBr (8.4 mg, 0.058 mmol) and 2,2'-bipyridine (18.4 mg, 0.12 mmol) in water in oxygen-free conditions and 0.20 ml of the catalyst stock solution was added to the Schlenk tube to start the polymerization. The reaction was stopped after 2 hours by diluting with water. The product was then purified by dialysis.

Polymerizations were conducted using a 0.4 g albumin sample. However, the process is readily scalable to larger quantities. Homopolymers of NIPAAm were prepared, although many different polymer compositions and architectures, including block and graft copolymers may be synthesized using this or other polymerization techniques.

Example 2

Polymerization from BSA that was Reduced Prior to Conjugation of the Initiator, with or without Addition of a Non-Interacting Initiator Preparation of the Bovine Serum Albumin (BSA) Macroinitiator. While BSA contains a free cysteine, it is known that partial oxidation at Cys-34 results in only about 50% of the residue being available for conjugation. Therefore, to maximize the number of thiols present for initiator conjugation, BSA was first reduced with tris-(2-carboxyethyl) phosphine hydrochloride (TCEP). Quantification using Ellman's assay (Harnanson, G. T., *Bioconjugate Techniques*, Academic Press, NY, (1996)) confirmed that, after reduction, the average percentage of free thiols was increased from approximately 50% to about 300%. This indicates that one disulfide bond in the protein was cleaved and that three thiols now were available per BSA molecule for subsequent conjugation to the thiol reactive pyridyl disulfide initiator (1 in FIG. 4).

Figure 4:
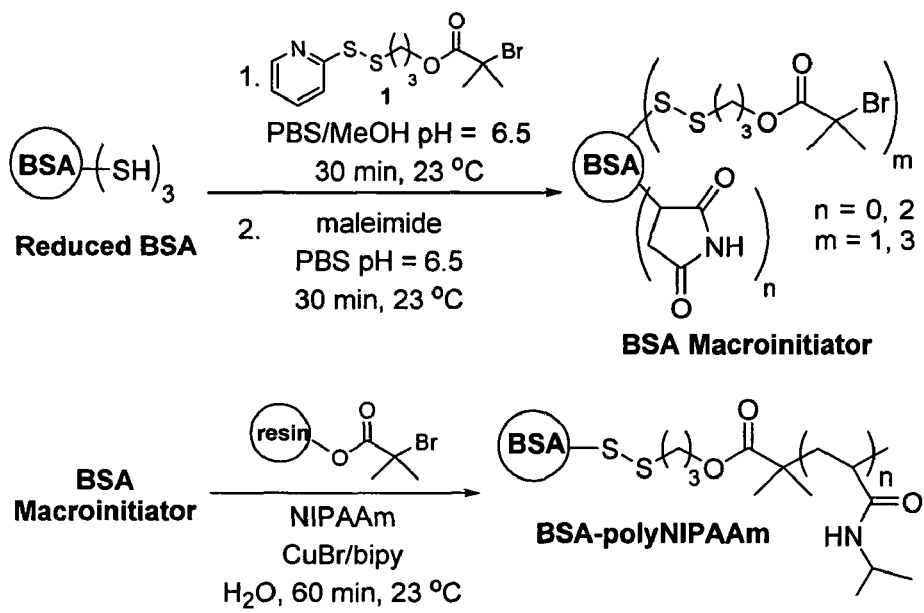
FIG. 4 shows a second reaction scheme for modification of bovine serum albumin in the presence of a 2-bromoisobutyrate-functionalized resin.

FIG. 4 shows the reaction scheme for the modification of BSA with the initiator fragment followed by capping to form a BSA macroinitiator, followed by polymerization in the presence of 2-bromobutyrate-functionalized resin. A solution of the thiol reactive pyridyl disulfide initiator (1) in methanol was added to the reduced BSA in phosphate-buffered saline (PBS) and stirred under argon for 30 min to form the disulfide-linked conjugate. Thiols are excellent chain transfer agents and therefore unmodified cysteines can be detrimental to the subsequent polymerization reaction. Although this is unlikely to be problematic when small amounts of protein are utilized, to exclude this possibility the resulting BSA-initiator conjugate was reacted with maleimide to "cap" any unmodified thiols (FIG. 4). Ellman's assay confirmed that free thiols were no longer present, which meant that every cysteine was reacted with maleimide, or reformed a disulfide bond. Electrospray ionization mass spectrometry (ESI-MS) was employed to monitor each step of the reaction; the results confirmed that BSA was modified with initiation sites. Intense peaks at masses 66,680 amu and 66,869 amu were observed for the BSA macroinitiator corresponding to BSA modified with one initiator, without and with maleimide conjugation, respectively. The protein with three initiators was also detected (67,157 amu), indicating that BSA with either one or three polymer chains attached was possible after polymerization. Tandem mass spectrometry analysis (μLC-MSMS) of the trypsin digest peptides for the BSA-macroinitiator showed that Cys-34 was modified with the initiator. The monoisotopic masses of the peptide fragment containing Cys-34 derived from the macroinitiator and unmodified BSA were 2674.21 and 2435.25 amu, respectively. The difference (238.96 amu) corresponded exactly to the expected mass of the initiator.

Polymerization from BSA. Polymerization from a protein in the presence of an added initiation agent was undertaken to demonstrate that the technique is suitable for small scale procedures, for example when only small quantities of biomolecule are available. BSA was modified with a 2-bromoisobutyrate group, a typical initiator for ATRP, to start the polymerization from defined sites on the protein as shown in FIG. 4, to form a BSA macroinitiator. NIPAAm was then polymerized from the BSA macroinitiator in water at ambient temperature (reaction (b) of FIG. 4) using the catalyst system copper bromide/2,2'-bipyridine (CuBr/bipy) in the presence of a 2-bromoisobutyryl-functionalized resin. The initial ratio of [NIPAAm]/[resin]/[CuBr]/[bipy], where [resin] indicates the estimated concentration of initiating sites on the resin, was 100:1:1:2. The "sacrificial" resin-bound initiator increased the total initiator concentration and thus enabled polymerization at very low macroinitiator concentrations. Because many proteins are available only in small quantities, flexibility in this respect is essential. However, BSA is commercially available in large quantities, and therefore polymerization without the "sacrificial" initiator was also demonstrated with an initial [NIPAAm]/[BSA macroinitiator]/[CuBr]/[bipy] ratio of 254:1:1:2. Removal of the polymer-coated resin from the protein-polymer conjugate after the polymerization was easily achieved by centrifugation, and for both polymerizations, the characteristic thermal precipitation of the polyNIPAAm allowed for immediate detection of conjugate formation. Analysis of the crude reaction mixtures by SEC showed that 65% of the BSA was modified to form a polyNIPAAm-conjugate. Polymerization in the absence of the "sacrificial" resin resulted in 44% of BSA-polyNIPAAm conjugate. Conjugate formation was also verified by SDSPAGE.

Two control experiments were performed on this system. First, NIPAAm was polymerized from the initiator-functionalized resin in the presence of maleimide-capped BSA, and second, unmodified BSA was incubated with NIPAAm monomer and the catalyst to determine if the polymerization could be initiated in the absence of the 2-bromoisobutyrate group. Analysis by SDS-PAGE indicated that in both cases polymer had not formed and the protein after polymerization did not shift to higher molecular weight. These results indicate that the bioconjugate does not form via chain transfer reactions and that the protein must be modified with initiation sites for polymerization to occur.

Characterization of BSA-polyNIPAAm Conjugates and Polymer. Prior to product isolation, GPC studies were carried out to rule out the presence of any free polyNIPAAm in solution. Small aliquots of the reaction mixture obtained after polymerization were lyophilized and then redissolved in DMF. Because BSA is insoluble and polyNIPAAm is soluble in DMF, any possible free polymer remaining could be selectively extracted. In both cases, polymer was not observed by GPC, indicating that no free polyNIPAAm was formed in solution. Therefore, the thermosensitivity observed were due to polymer being covalently attached to BSA.

Figure 5:
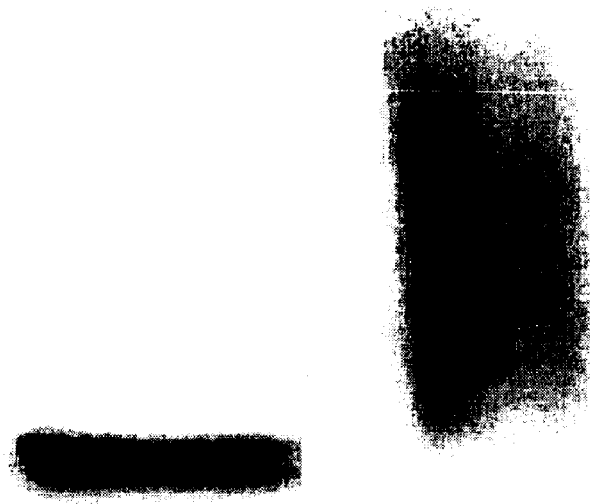
FIG. 5 shows an SDS-PAGE analysis of the conjugate formed by the reaction scheme of FIG. 4.

Because of the differences in retention times for the reactants and end product, isolation of the BSA-polymer conjugates from unmodified BSA and unreacted monomer was accomplished by preparative SEC. After purification of the conjugate prepared in the presence of "sacrificial initiator," only a small amount of unmodified BSA was present in the conjugate sample, demonstrating the effectiveness of the purification procedure. After lyophilization, this conjugate was analyzed by SDS-PAGE (FIG. 5). Under nonreducing conditions (the right column) the conjugate appeared as a broad band higher in molecular weight than BSA. The sample was also heated in the presence of the reducing agent β-mercaptoethanol and then analyzed. Under these conditions, the polymer was cleaved from the protein and only the BSA band was visible in the SDS-PAGE gel (the left column of FIG. 5). These results indicate that, as expected, the polymer is conjugated to the protein via a reversible disulfide bond.

Figure 6:
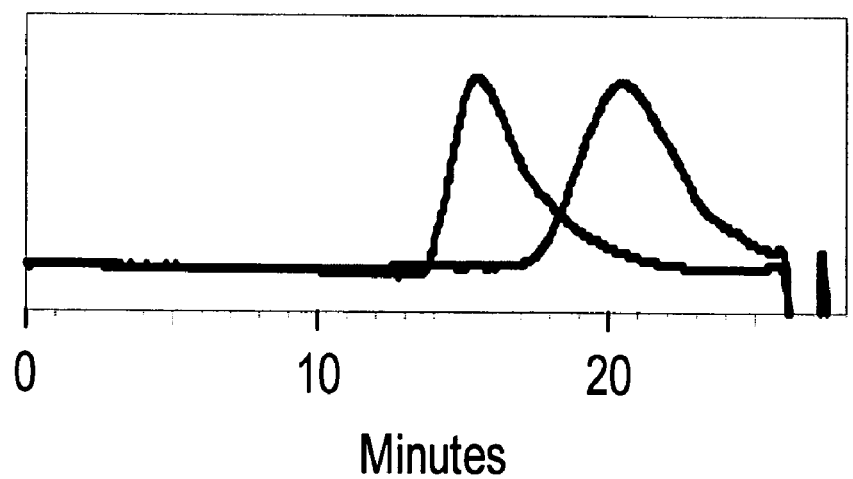
FIG. 6 compares the GPC trace of isolated poly NIPAAm polymerized in the presence and absence of resin.

The disulfide linkage was exploited to isolate and characterize the polymer formed on the protein. PolyNIPAAm was cleaved from the BSA-polyNIPAAm conjugate by treating the conjugate with a 1 mg/mL solution of a reducing agent, dithiothreitol (DTT), in DMF for 3 days at 60° C. DMF was used to avoid precipitation of the polymer. GPC traces (FIG. 6) of the cleaved polymers (the right curve is in the presence of resin; the left curve is without resin) exhibited low molecular weight tailing which can be attributed to termination reactions early in the polymerization. Nevertheless, the chromatograms were monomodal. Polydispersity indices of the polyNIPAAm polymerized in the presence and absence of resin were 1.34 (number average molecular weight=11,300) and 1.50 (number average molecular weight=58,300), respectively. The identity of the polyNIPAAm was confirmed by $^1$H NMR analysis.

For comparison, polymerization of NIPAAm in water was evaluated using a water soluble 2-bromoisobutyryl oligo(ethylene glycol) initiator under similar reaction conditions used for the polymerization/conjugation of BSA. Polymerized NIPAAm had a polydispersity of 3.25. Although a different catalyst was employed (copper chloride/bipy) this does not explain the differences in molecular weight distribution. It was concluded that that the lower polydispersity obtained when polymerizing from the protein macroinitiator is due to site isolation of the growing radicals on the BSA, thereby reducing termination events, which ultimately results in the narrower molecular weight distributions for the polymer. In addition, polymers in solution can freely diffuse, and thus the rate of termination should be faster compared to protein-bound polymer. Differences in diffusion have in the past been attributed to differences in termination rates for polymers in solution versus those grown from nanoparticles.

Taken together, the results clearly demonstrate that proteins modified with initiation sites through disulfide bonds can be used as macroinitiators for polymerization. The resulting conjugates are readily purified, and the polymers formed have narrower molecular weight distributions than those polymerized under similar conditions in solution. No free polymer is detected at the end of the polymerization, and the polymer is released under reducing conditions indicating that the polymer is conjugated to the protein through a disulfide bond.

Example 3

Modification of Lysozyme Mutant V131C

Figure 7:
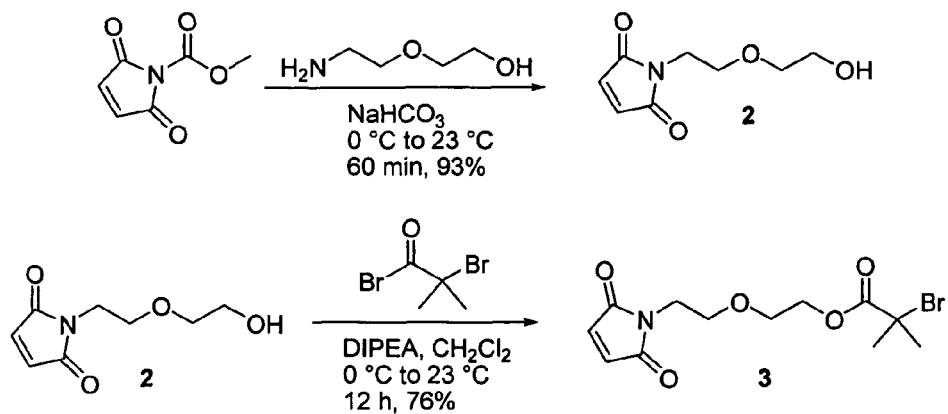
FIG. 7 shows a reaction scheme for synthesis of a maleimide-functionalized initiator.

The bioactivity of the protein-polymer conjugate can be important for some applications. Therefore to readily access the bioactivity of the conjugates after formation of the polymer, modification of an enzyme was also demonstrated. A genetically engineered "V131C" mutant of T4 lysozyme, bearing a single cysteine that conferred one free thiol to the protein for subsequent modification was utilized. Employing *E. coli* host BL21(DE3) and the expression vector for V131C, the mutant was expressed and isolated as described by Hubbell and co-workers (Mchaourab, H. S., Lietzow, M. A., Hideg, K., Hubbell, W. L. *Biochemistry*, 35 p7692-7704 (1996); Columbus, L., Kalai, T., Jeko, K., Hideg, K., Hubbell, W. L. *Biochemistry*, 40 p3828-3846 (2001)) and then purified by cation exchange chromatography and preparative SEC. SDS-PAGE under reducing and nonreducing conditions indicated that the mutant was isolated as a mixture of dimer and monomer. Therefore, initiator conjugation was preceded by reduction using immobilized TCEP disulfide reducing gel. The single cysteine of lysozyme mutant V131C (hereafter referred to as "lysozyme") was modified via a disulfide bond using the pyridyl disulfide initiator (Compound 1 in FIG. 4) or through an irreversible C—S bond using the maleimide end-functionalized initiator (Compound 3 in FIG. 7). The maleimide initiator 3 was synthesized in two steps from commercially available N-methoxycarbonyl maleimide. Maleimidoethoxyethanol (Compound 2 in FIG. 7) was synthesized following the procedure of Weber et. al. (Weber, R. W., Boutin, R. H., Nedelman, M. A., Liszter-James, J, Dean, R. T., *Bioconjugate Chem.*, 1, p431-7 (1990)) and then esterified with 2-bromoisobutyryl bromide in the presence of N,N-diisopropylethylamine to form the maleimide end-functionalized initiator 3 with a 76% yield (FIG. 7).

Figure 8:
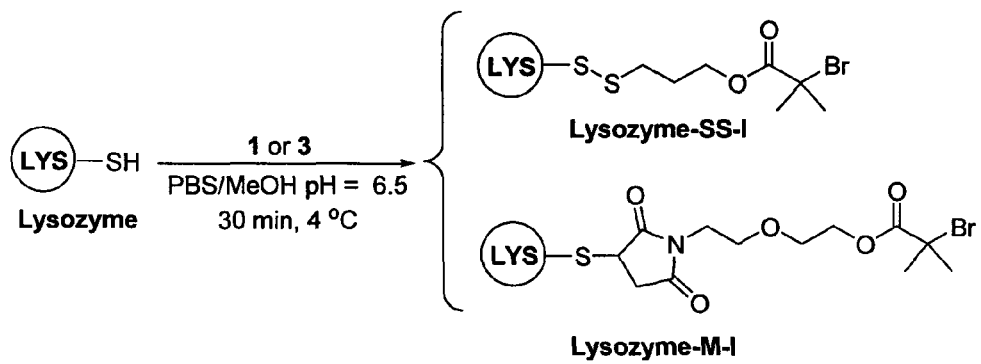
FIG. 8 shows the reaction scheme for the conjugation using one or the other of two different initiators to form two different modified lysozymes.

Conjugation of the two initiators to lysozyme proceeded by mixing the enzyme in PBS (pH 6.5) with a solution of either the pyridyl disulfide initiator (Compound 1 in FIG. 4) or maleimide end-functionalized initiator (Compound 3 in FIG. 7) in MeOH at 4° C. for 30 min (FIG. 8). Using ESI-MS on the products it was confirmed that in both cases the lysozyme was modified with one initiator. Intense peaks at 18,848 amu for the disulfide-initiator-modified lysozyme and at 18,942 amu for the maleimide-modified lysozyme were observed. No unmodified protein was detected. A trypsin digestion was performed on the lysozyme-disulfide initiator. The high cross correlation coefficient (2.88) obtained from the peptide fragment containing the Cys-131 indicated that the lysozyme was indeed modified at the cysteine residue and not through covalent attachment to a different amino acid residue of the protein.

Figure 9:
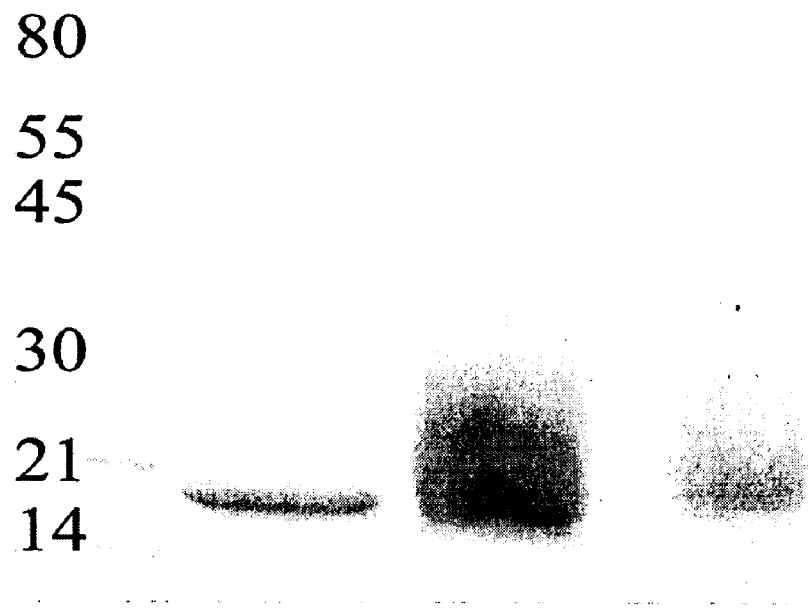
FIG. 9 shows an SDS-PAGE analysis of lysozyme (left) and the crude lysozyme-poly NIPAAm conjugates (middle and right).
Figure 10:
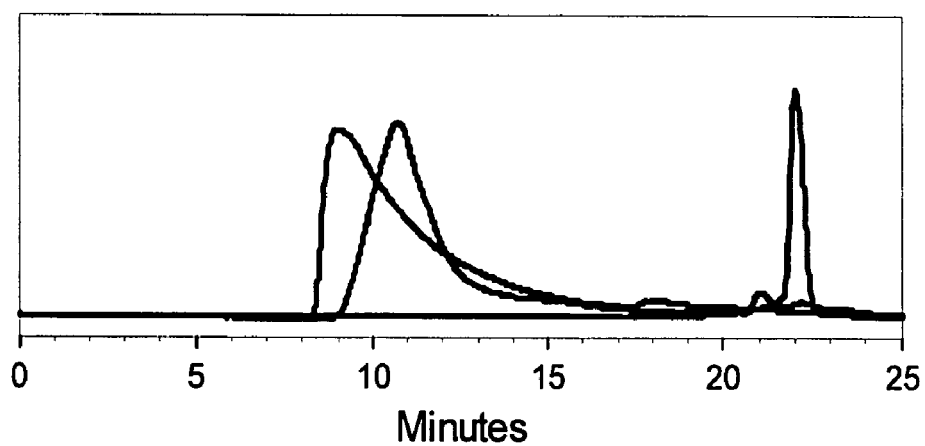
FIG. 10 shows isolated SEC traces for lysozyme-SS-poly NIPAAm, lysozyme-m-poly NIPAAm and lysozyme.

Polymerization from lysozyme was then conducted in water at ambient temperature in the presence of functionalized resin in the same manner described above using the BSA macroinitiator in the presence of the noninteracting initiator. After 90 minutes the reaction mixture was exposed to air to stop polymerization, and the resin was removed by centrifugation. Analysis of the crude lysozyme-polyNIPAAm conjugates by SEC showed that polymerization from the disulfide macroinitiator resulted in approximately 75% protein-polymer conjugate formation, and polymerization from the maleimide macroinitiator resulted in a yield of about 65% protein-polymer conjugate. The analysis of the crude conjugates by SDS-PAGE is shown in FIG. 9. A higher molecular weight band was apparent for both of the lysozyme conjugates compared to that of the unmodified lysozyme. Purification of the conjugates was achieved by preparative SEC, and the traces of the isolated conjugates were significantly shifted to higher molecular weight compared to that of unmodified lysozyme. FIG. 10 is a graph showing isolated SEC traces for lysozyme-SS-polyNIPAAm (left curve), lysozyme-M-polyNIPAAm (middle curve) and unmodified lysozyme (right curve).

Activity of Resultant Lysozyme-polyNIPAAm Conjugates. Lysozyme is a small enzyme that provides protection from bacteria by breaking down polysaccharide walls. The enzymatic activity of the lysozyme-polyNIPAAm was assessed and compared to that of unmodified mutant lysozyme to demonstrate that bioactivity is unaffected by the polymerization process. The results illustrate that the lysozyme survives the polymerization conditions and that bioactivity is unaffected by polymer conjugation.

Figure 11:
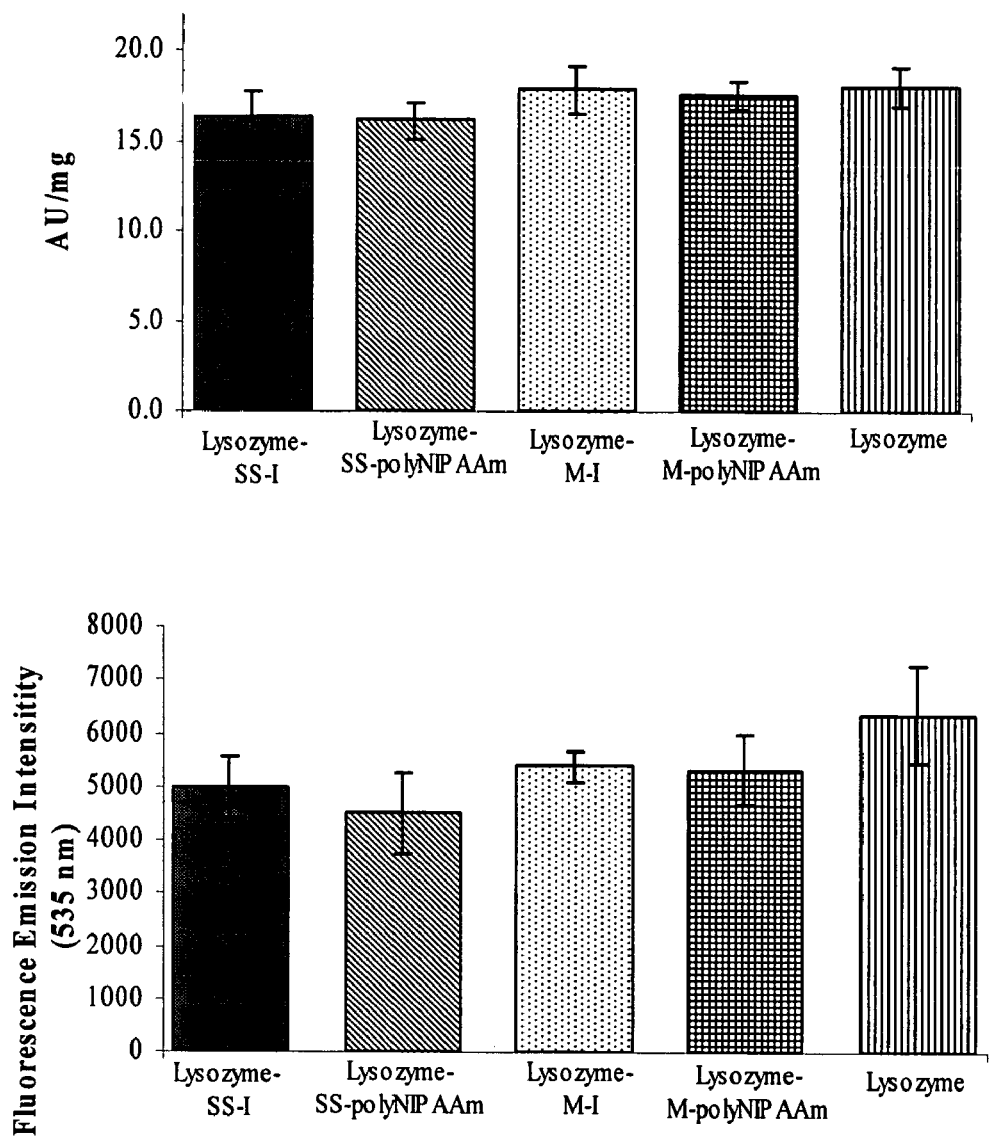
FIG. 11 compares the activity of 5 different compositions using UV-vis and fluorescence assays.

The activities of the conjugates were evaluated using standard assays and compared to that of the unmodified lysozyme. The first assay measured the lytic ability of the lysozyme with respect to the lyophilized substrate *Micrococcus lysodeikticus*. Lysozyme, lysozyme initiators, and isolated lysozyme conjugates were prepared with equal protein concentrations, and then 100 µL of the enzyme solution was mixed with 600 µL of *M. lysodeikticus* solution. Upon cell wall lysis, the solution becomes less turbid, and this decrease in absorbance was monitored for 2 min. at 450 nm. Activity was expressed in activity units (AU). One AU is defined as a change in absorbance of 0.001 per min. These experiments were performed 4 times for each sample. The materials are compared in the upper portion of FIG. 11 using one-way analysis of variance (ANOVA). No statistical difference in activities between the various materials tested (Lysozyme-SS-I, lysozyme-SS-polyNIPAAm, Lysozyme-M-I, lysozyme-M-polyNIPAAm and Lysozyme) was observed ($P>0.10$).

The second activity assay performed on the lysozyme conjugates measured the lytic activity toward fluorescein-labeled *Micrococcus lysodeikticus*. Following the manufacture's protocol, in a 384-well plate, lysozyme samples of equivalent protein concentrations were incubated with the labeled substrate for 30 min. at 37° C. Fluorescence emission at 535 nm (excitation at 485 nm) was measured, and the average intensities (triplicate experiments) were compared (lower graphs in FIG. 11). One-way ANOVA analysis indicated no statistical difference between the samples ($P>0.07$). It is therefore concluded that conjugation of the lysozyme with an initiator for polymerization, or with an eventual polymer, does not result in a decrease of enzyme activity and bioactivity was retained.

Example 4

Figure 12:
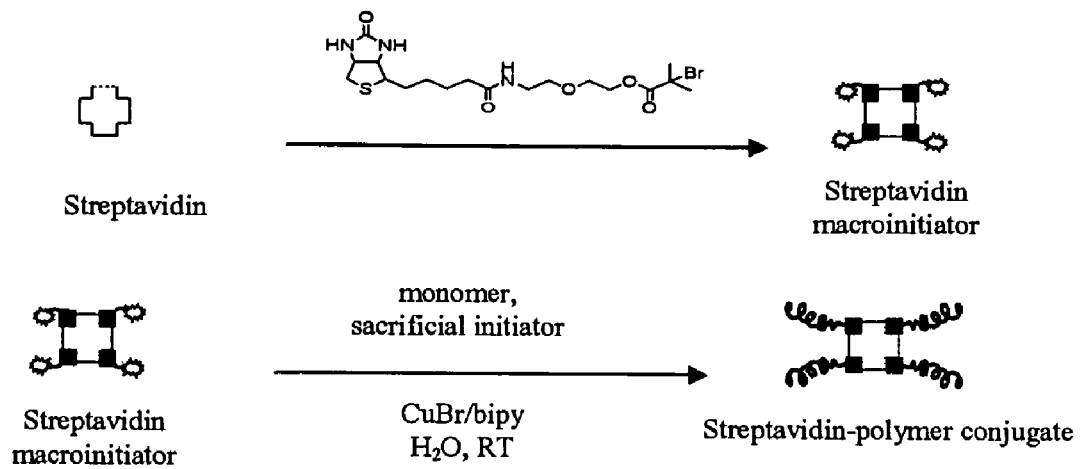
FIG. 12 is a schematic diagram illustrating the formation of a streptavin-polymer conjugate.

Polymerization from Streptavidin Modified with a Biotinylated Initiator in the Presence of Non-Interacting Initiator Streptavidin (SAv) is a well-studied protein that consists of four subunits, each of which is capable of binding one molecule of biotin with very high affinity ($K_d=10^{-15}$ M. The general procedure for conducting polymerizations from streptavidin is outlined in FIG. 12. Modification of SAv with an opportune initiator was used to achieve polymer formation. A biotinylated ATRP initiator described by Qi et al (Qi, K., Ma, Q., Remsen, E. E., Clark, C. G., Jr. Wooley, K. I, *J. Am. Chem. Soc.*, 126, p 6599-6607 (2004)) was prepared and interacted with SAv to generate the protein macroinitiator.

Figure 14:
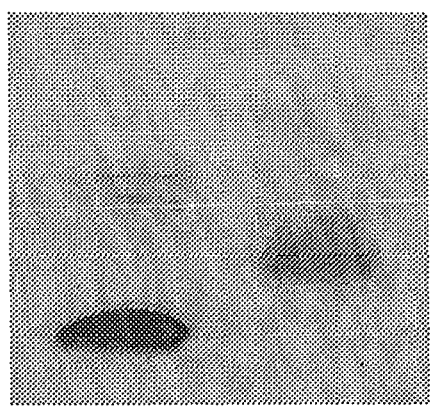
FIG. 14 shows the gel electrophoresis separation of streptavidin (Column A) and poly(N-isopropylacrylamide)-streptavidin conjugate (Column B) obtained by polymerizing streptavidin previously modified with a biotinylated initiator.

Polymerization from the protein in the presence of an added non-interacting initiation agent was undertaken. As an illustrative example, streptavidin was interacted with the bromoisobutyrate-modified biotin initiator shown in FIG. 13. This biotin initiator binds with very high affinity to streptavidin. Polymerization with NIPAAm was initiated from the modified streptavidin with simultaneous initiation from a non-interacting bromoisobutyrate-modified solid phase Wang resin. The non-interacting initiator does not bind to the protein, and the polymer grown from this initiator is not bound to the protein. The resulting polymer-modified Wang resin could be readily removed, leaving the streptavidin-polymer conjugate in solution. A similar, but reversed, concept has been employed in surface-initiated ATRP, where additional soluble initiator has been successfully employed to increase the concentration of initiating sites and thus allow the system to self-equilibrate via persistent radical effect. The polymerization was performed on 1.0 mg of SAv macroinitiator using a NIPAAm/total initiator ratio of 100:1. Polymerization from streptavidin was evidenced by the higher molecular weight of the conjugate, as shown by gel electrophoresis (FIG. 14).

Initiation from a very small amount of biomolecule (<10 mg) without added non-interacting initiator may be difficult because the initiator would be very dilute. However the non-interacting initiator circumvents this by effectively increasing the number of initiation sites in the polymerization mixture. As an illustrative example, an insoluble initiator was chosen that is easily filtered away at the end of the reaction. However a soluble initiator may be used in the alternative.

Synthesis of the Biotinylated Initiator

Biotin (1.500 g, 6.14 mmol) and N,N'-disuccinimidyl carbonate (1.573 g, 6.14 mmol) were dissolved in 25 mL of dry DMF in argon atmosphere. Triethylamine (0.745 g, 7.37 mmol) was added and the mixture stirred at room temperature for 6 hours. 2-(2-Aminoethoxy)ethanol (0.646 g, 6.14 mmol) was then added and the reaction was allowed to proceed at room temperature overnight. The DMF was then evaporated under reduced pressure, the product was dissolved in methanol and the insoluble residue was filtered out. A fraction of the pure product (400 mg, isolated after two recrystallizations from methanol/ether 1:2) was then dissolved in dry DMF (10 mL). 2-Bromo-2-methylpropionic acid (300 mg, 1.8 mmol), N,N'-dicyclohexyl-carbodiimide (371 mg, 1.81 mmol) and DMAP (29.5 mg, 0.24 mmol) were then added and the mixture was stirred overnight at room temperature. The precipitate which formed was filtered out. After evaporating the DMF under reduced pressure, the residue was purified by column chromatography (dichloromethane:methanol=9:1) producing the initiator shown in FIG. 13 in a yield of about 52%.

Synthesis of the Non-Interacting Initiator.

A two neck round-bottomed flask was charged with Argo-Gel Wang polymer beads (Aldrich, 240 mg, 0.084-0.108 mmol of hydroxyl groups), 2-bromo-2-methylpropionic acid (541 mg, 3.24 mmol) and DMAP (79.2 mg, 0.648 mmol) in argon atmosphere. Dry DMSO (7.5 mL) and 1,3-diisopropylcarbodiimide (500 mL, 3.24 mmol) were added and the mixture was stirred at room temperature overnight. The polymer beads, which now carried the non-interacting initiator, were then filtered out and extensively washed with DMSO, water and THF and dried under high vacuum. The presence of the initiator fragment on the beads was verified by IR spectroscopy ($V_{COOR}$=1731 cm$^{-1}$).

Modification of Streptavidin with the Non-Covalent Initiator: Conjugation of the 2-bromoisobutyrate Biotinylated Initiator to Streptavidin.

Streptavidin (4.05 mg) was dissolved in 2 mL of phosphate buffer, pH 7.0. A methanol solution of 2-bromoisobutyrate biotinylated initiator shown in FIG. 13 (0.100 mL, containing 1.8 mg of biotinylated initiator) was slowly added to the streptavidin solution. The mixture was incubated at room temperature for 1 hour. The product was then purified by dialysis and recollected after lyophilization.

Polymerization from Small Amounts of Streptavidin-2-Bromoisobutyrate.

A flask was charged with the beads carrying the non-interacting initiator (10 mg, 0.0035-0.0045 mmol of initiating groups) and N-isopropylacrylamide (NIPAAm, 51 mg, 0.45 mmol). The system was then evacuated and refilled with argon three times and a deoxygenated solution of streptavidin (0.700 mg) modified with the biotinylated initiator in water was added. Polymerization on the beads was initiated by adding 0.050 mL of a CuBr/2,2'-bipyridine stock solution (prepared dissolving 6.4 mg of CuBr and 14.0 mg of 2,2'-bipyridine in 0.500 mL of degassed water). The reaction was stopped after 40 minutes by opening the flask to air and separating the streptavidin solution from the beads by filtration. The protein-polymer conjugate was purified from the catalyst and the unreacted monomer by dialysis.

Figure 15:
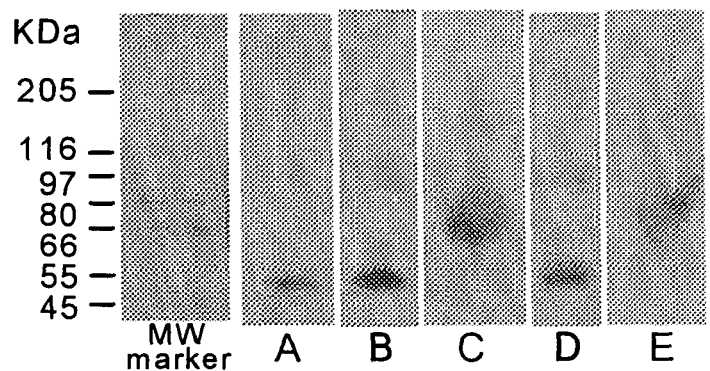
FIG. 15 is a comparison of SDS-PAGE gel separation of 5 different streptavidin materials.
Figure 16:
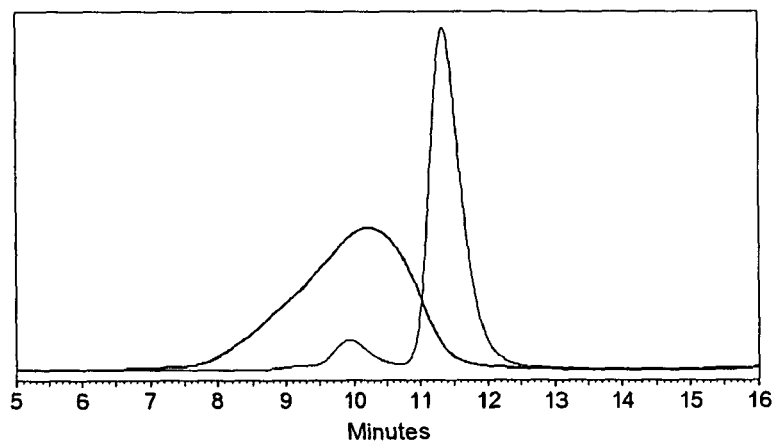
FIG. 16 is graph contrasting the SEC chromatograph for streptavidin macroinitiator with the curve for streptavidin-poly NIPAAm conjugate.

FIG. 15 Compares the SDS-PAGE gel results for five materials—SAv (Column A), SAv-macroinitiator (Column B), SAv-polyNIPAAm in the presence of sacrificial initiator (Column C), SAv-biotin control polymerization (Column D) and SAv-polyPEGMA (Column E). FIG. 16 is an SEC chromatograph comparing the SAv-polyNIPAAm conjugate formed in the presence of sacrificial initiator (left curve) with SAv-macroinitiator (right curve) (10 mM ammonium acetate and 100 mM sodium chloride buffer, pH=6.6, flow rate=0.25 mL/min, λ=290 nm). Conjugate formation was evident by shifts to higher molecular weight in both the SDS-PAGE gel (FIG. 15, column C) and SEC chromatograph (FIG. 16). No unmodified SAv was detected meaning that at least one site per protein had initiated. In addition, the conjugate precipitated when the solution was heated which is behavior typical of poly-(NIPAAm)-protein conjugates.

Control experiments were performed by exposing SAv or SAv-biotin not modified with the ATRP initiator to identical polymerization conditions in the presence of the sacrificial initiator. Polymerization proceeded from the solid resin as evidenced by FTIR, but as expected, no protein-polymer conjugates were detected by SDS-PAGE (FIG. 15, Column D), mass spectrometry, or SEC. These results illustrate that polymerization proceeds only when the protein is modified with initiator.

To further confirm that poly(NIPAAm) is formed and is attached to SAv at the biotin binding sites only, the polymerization was repeated with 5 mg of macroinitiator, and the conjugate was isolated. Treatment of the SAv-polymer conjugate with DMF/water at 90° C. for 1 h resulted in dissociation of the protein into monomeric subunits and simultaneous release of the polyNIPAAM. SDS-PAGE demonstrated that all SAv had dissociated, and the shift in the gel was identical to the monomeric subunits of unmodified SAv. The latter indicates that polymer is not covalently attached to amino acid residues but rather through the biotin-streptavidin non-covalent interaction.

The identity of the isolated polymer was confirmed by $^1$H NMR. Gel permeation chromatography (GPC) resulted in a monomodal peak with a number-average molecular weight (Mn) of 27,000 and polydispersity index (PDI)=1.7. The broad PDI is not uncommon for ATRP in pure water and indicates poor control over the polymerization. Although the presence of biotin was difficult to observe by $^1$H NMR, biotinylation was confirmed using surface plasmon resonance (SPR) by passing the polymer solution over a SAv-coated chip. Binding of the polymer to the surface was clearly observed, demonstrating that the polyNIPAAm is biotinylated. Taken together, these results show that bioconjugate formation results from polymerization initiated at only the biotin binding sites of the macroinitiator.

The flexibility of the strategy was also demonstrated by the polymerization of the initiator-modified SAv with other monomers such as poly(ethylene glycol) methyl ether methacrylate. In particular, conjugates containing poly(ethylene glycol) methyl ether methacrylate (PEGMA) and SAv initiator (1.0 mg) (PEGMA/total initiator≈140:1) were formed in the presence of sacrificial initiator (FIG. 15, Column E). This is of interest because of the utility of the conjugate in drug delivery systems and protein-repellent materials.

Using a modified SAv as an initiator for the polymerization with NIPAAm it has been demonstrated that the protein is quantitatively modified with polymer formed in situ and that the resulting polymer is conjugated to the SAv at the biotin binding sites only. Streptavidin retains its bioactivity after subjection to polymerization; no monomeric subunits were observed, and the protein still binds biotin. This straightforward approach can be applied to a variety of monomers, including PEGMA to form the biologically relevant biomolecule conjugates.

The results verify with three different systems, BSA, lysozyme and streptavidin that protein-polymer conjugates can be prepared by polymerization of the monomer with modified proteins. The initiation site can be linked through a disulfide bond or through an irreversible C—S bond or other selectively modified sites on the biomolecule. The polymerizations can be conducted in the presence or absence of a non-interacting initiator. Furthermore, the preparative conditions are not detrimental to bioactivity as demonstrated by retention of the enzymatic activity of lysozyme after polymerization and retention of streptavidin activity, namely biotin binding. Cysteines are used as reaction sites to produce well-defined conjugates. It has now been demonstrated that proteins can be modified through cysteine residues and utilized as macroinitiators for polymerization. These results provide evidence that this strategy, which has many advantages over traditional synthetic methods which require the polymer first be formed before conjugation, is a flexible approach to preparing bioactive protein-polymer conjugates. The process is not limited to providing bromoisobutyrate functionality or the polymerization with acrylamides and other combinations of initiators and monomers reactive therewith can be used. Proteins may be modified to have an initiation site or prepared with an initiation site by incorporation of amino acids suitable for polymer initiation. The same general approach, using radical polymerization chemistry, can be used for the preparation of conjugates with many different proteins, enzymes and antibodies leading to functional materials. This technique can be readily extended to other proteins. In addition, the procedure and methods described herein are not limited to proteins, enzymes and antibodies and may be applied to a broad range of biomolecules. Also, while ATRP is indicated as a preferred technique other controlled radical polymerization techniques may also be used. One skilled in the art will recognize, based on the techniques and procedures set forth herein, other polymerization techniques exist which can be used to react a biomolecule having activated or reactive sites thereon with a monomer to form a conjugate thereof.

The above examples are merely representative of the processes described herein. Based on the teachings herein, one skilled in the art will recognize that protein-polymer conjugates can be formed from many different proteins by providing modified proteins and then reacting the modified proteins with monomers to generate the conjugate. One skilled in the art will also recognize that the methods taught herein can also be applied to the formation of polymer conjugates with a wide range of biomolecules such as enzymes or antibodies.

We claim:

1. A protein-polymer conjugate comprising a single protein with initiator-modified locations thereon, said protein modified to include one or more bromoisobutyrate-modified ligand initiators, one or more polymer chains bound to the protein with each initiator-modified location forming a link between the single protein and a single polymer chain, the protein-polymer conjugate formed by reacting the initiator-modified locations on the protein each with a monomer and polymerizing to form the conjugate wherein the monomer is poly(ethylene glycol) methyl ether methacrylate.

2. The protein-polymer conjugate of claim 1 wherein the initiator is a bromoisobutyrate-modified biotin initiator.

3. The protein-polymer conjugate of claim 1 wherein the protein is streptavidin.

4. A method of forming a protein-polymer conjugate comprising modifying a protein to have functionality suitable for initiation of radical polymerization and reacting the modified protein with a monomer comprising:

modifying the protein by interacting with a bromoisobutyrate-modified ligand initiator, mixing said protein modified by the bromoisobutyrate-modified ligand initiator with a non-interacting bromoisobutyrate-modified solid phase resin and adding to said mixture a suitable reactive monomer under conditions suitable to initiate polymerization of the protein modified by the bromoisobutyrate-modified ligand initiator with the monomer to form the protein-polymer conjugate.

5. The method of claim 4 wherein the initiator is a bromoisobutyrate-modified biotin initiator.

6. The method of claim 4 wherein the protein is streptavidin.

7. The method of claim 4 wherein the monomer is N-isopropylacrylamide.

8. The method of claim 4 wherein the monomer is poly(ethylene glycol) methyl ether methacrylate.

* * * * *